(12) United States Patent
Li et al.

(10) Patent No.: US 8,197,838 B2
(45) Date of Patent: Jun. 12, 2012

(54) SUSTAINED RELEASE SYSTEMS OF ASCORBIC ACID PHOSPHATE

(75) Inventors: Yufu Li, Bridgewater, NJ (US); Stephen Wohlert, Norderstedt (DE); Chunlin Yang, Belle Mead, NJ (US)

(73) Assignee: Advanced Technologies and Regenerative Medicine, LLC., Raynham, MA (US)

( * ) Notice: Subject to any disclaimer, the term of this patent is extended or adjusted under 35 U.S.C. 154(b) by 0 days.

(21) Appl. No.: 13/006,586

(22) Filed: Jan. 14, 2011

(65) Prior Publication Data

US 2011/0104232 A1    May 5, 2011

Related U.S. Application Data

(62) Division of application No. 12/332,414, filed on Dec. 11, 2008, now Pat. No. 8,034,363.

(51) Int. Cl.
| | | |
|---|---|---|
| *A61K 31/665* | (2006.01) | |
| *A61K 9/70* | (2006.01) | |
| *A61K 35/12* | (2006.01) | |
| *A61P 17/02* | (2006.01) | |
| *A61P 19/00* | (2006.01) | |

(52) U.S. Cl. .......................... 424/423; 514/99; 424/93.7
(58) Field of Classification Search .................. None
See application file for complete search history.

(56) References Cited

U.S. PATENT DOCUMENTS

| | | |
|---|---|---|
| 5,140,043 A | 8/1992 | Darr |
| 5,578,471 A | 11/1996 | Fujio |
| 6,491,948 B1 | 12/2002 | Buchholz |
| 7,666,410 B2 | 2/2010 | Lye |
| 2002/0019372 A1 | 2/2002 | Schnellmann |
| 2004/0001878 A1 | 1/2004 | DeBusk |
| 2004/0193274 A1 | 9/2004 | Trieu |
| 2006/0246121 A1 | 11/2006 | Ma et al. |
| 2008/0058410 A1 | 3/2008 | Kim |
| 2008/0274185 A1 | 11/2008 | Mao |
| 2010/0150981 A1 | 6/2010 | Li |
| 2010/0272782 A1 | 10/2010 | Owens |

FOREIGN PATENT DOCUMENTS

| | | |
|---|---|---|
| WO | WO 9940990 A1 | 8/1999 |
| WO | WO 0124842 | 4/2001 |
| WO | WO0215860A1 A1 | 2/2002 |
| WO | WO 02100462 | 12/2002 |
| WO | WO 2004101764 | 11/2004 |
| WO | WO 2006032092 | 3/2006 |
| WO | WO 2006047310 | 5/2006 |
| WO | WO 2006066227 A2 | 6/2006 |
| WO | WO 2006133506 | 12/2006 |
| WO | WO 2007089864 | 8/2007 |
| WO | WO 2007089878 | 8/2007 |
| WO | WO2008155512A2 A2 | 12/2008 |
| WO | WO2010111108A2 A2 | 9/2010 |
| WO | WO2010128281A2 A2 | 11/2010 |
| WO | WO2010128281A3 A3 | 3/2011 |

OTHER PUBLICATIONS

Long C. L. et al: Ascorbic Acid Dynamics in the Seriously Ill and Injured, Journal of Surgical Research, (2003) 109, 144-148.
Kim H. et al : Sustained Release of Ascorbic-2-Phosphate and Deamethasone From Porous PLGA Scaffolds for Bone Tissue Engineering Using Mesenchymal Stem Cells, Biomaterials (2003) 24:4671-4679.
Shukla, S. P. Plasma and Urinary Ascorbic Acid Levels in the Postoperative Period. *Experientia* (1969) 25: 704.
Mason, M., Matyk, P. M., and Doolan, S. A. Urinary Ascorbic Acid Excretion in Postoperative Patients. *Am. J. Surg.*(1971) 122: 808.
Junge A. et al : Modification of Collagen Formulation Using Supplemented Mesh Materials, Hernia, (2006)10:492-497.
Levenson et al—Ascorbic Acid, Riboflavin, Thiamun, and Nicotinic Acid in Relation to Severe Injury, Hemorrhage, and Infection in the Human*, Vitamins in Acute Illness Annals of Surgery 24 (5) p. 840-856 1946.

*Primary Examiner* — Robert A Wax
*Assistant Examiner* — Danah Al-Awadi

(57) ABSTRACT

A novel method of preparing a controlled release composition is disclosed. Specifically, the present invention relates to a method of preparing controlled release compositions of ascorbic acid phosphate and absorbable polymers. Also disclosed is a novel controlled release composition of ascorbic acid phosphate made by the method of the present invention.

11 Claims, 4 Drawing Sheets

SUSTAINED RELEASE SYSTEMS OF ASCORBIC ACID PHOSPHATE

CROSS REFERENCE TO RELATED APPLICATION

This application is a divisional of application Ser. No. 12/332,414 filed on Dec. 11, 2008 now U.S. Pat. No. 8,034,363.

FIELD OF THE INVENTION

The invention relates generally to the field of controlled release compositions of ascorbic acid phosphate and their application for tissue repair and regeneration, in particular controlled release compositions of ascorbic acid phosphate and biodegradable polymers.

BACKGROUND OF THE INVENTION

Collagen is the major protein component of the extracellular matrix of all connective tissue, including skin, tendons, bones, cartilage, blood vessels and ligaments. It is well established that collagen plays a critical role in establishing and maintaining the structure of human tissues. Recent studies have revealed that collagen interacts with cells in connective tissues and transduces essential signals for regulation of cell anchorage, migration, proliferation, differentiation and survival.

It is well known that ascorbic acid is required for the hydroxylation of collagen. Ascorbic acid is a co-factor of prolyl hydroxylase and lysyl hydroxylase. Hydroxylation of proline is essential for the stabilization of collagen triple helix, while hydroxylation of lysine is required for collagen crosslinking. Compromised collagen production associated with ascorbic acid deficiency is believed to result in impaired wound healing, and may have other adverse effects.

Shukla, and Mason et al. (Shukla, S. P., *Plasma and Urinary Ascorbic Acid Levels in the Postoperative Period, Experientia* 25: 704, 1969) suggested that surgical stress resulted in increased ascorbic acid requirements. However, Levenson et al. (Levenson et al., *Vitamins in Acute Illness, Annals of Surgery* 24 (5) p 840-856 1946) reported plasma ascorbic acid levels below normal values in severely injured patients. In some patients, plasma levels of ascorbic acid were immeasurable within a few hours following major injury. Levenson et al. also reported that blood levels of ascorbic acid remained subnormal even with daily 1000 mg intramuscular injections through the eighth day. The incorporation of ascorbic acid into implantable devices and tissue engineering scaffolds for a localized and controlled release formulations of ascorbic acid in the sites where collagen biosynthesis is required would be desirable for enhancing tissue repair and regeneration.

Controlled release formulations of ascorbic acid phosphate have been prepared by solvent casting. For example, Hyongbum Kim et al. (Kim H. et al (2003): *Sustained Release of Ascorbic-2-phosphate and Deamethasone from Porous PLGA Scaffolds for Bone Tissue Engineering Using Mesenchymal Stem Cells, Biomaterials* 24:4671-4679) described a porous PLGA scaffold for controlled release of ascorbic acid phosphate, a stable form of ascorbic acid. The porous PLGA matrices containing ascorbic acid phosphate and dexamethasone were prepared by solvent casting/particulate leaching methods. There are disadvantages of using known solvent casting methods in preparing ascorbic acid phosphate controlled release formulations. The disadvantages include the need to remove residual solvent, the difficulty in or impossibility of preparing three dimensional (3-D) medical device parts by solvent casting, and there is a substantial burst of ascorbic acid phosphate release from solvent cast structures both in vivo and in vitro. Therefore, there is a need in this art for novel and improved methods for making ascorbic acid controlled release compositions, and medical devices and components made from such compositions.

SUMMARY OF THE INVENTION

The invention relates to a method of preparing a controlled release composition. Specifically, the invention relates to a method of preparing a controlled release composition of ascorbic acid phosphate.

The novel method of the present invention of making a novel controlled release composition of ascorbic acid phosphate has the following steps. Ascorbic acid phosphate is dried at a temperature of no greater than about 160° C. for about 30 minutes. The dried ascorbic acid phosphate is melt blended with an absorbable aliphatic polyester polymer at a temperature of no greater than about 160° C. to form an ascorbic acid phosphate and polymer composition. Optionally, the process has the additional step of processing the ascorbic acid and polymer composition into a desired form at a temperature of no greater than about 160° C.

Another aspect of the present invention is a novel ascorbic acid phosphate composition made by the above-described process. This novel composition may be further processed into medical devices or components by melt processing at a temperature no greater than 160° C.

Still yet another aspect of the present invention is a medical device manufactured from the controlled release compositions of the present invention.

These and other aspects and advantages of the present invention will become more apparent from the following description and accompanying drawings.

DETAILED DESCRIPTION OF THE INVENTION

Figure 1:
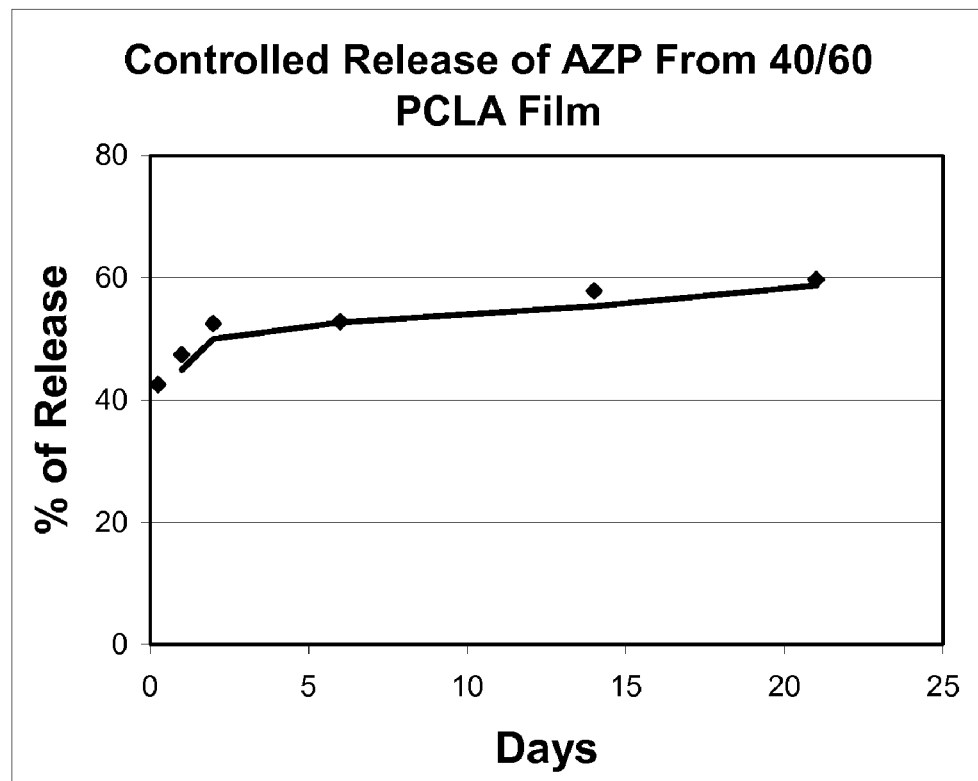
FIG. 1 shows a release profile of ascorbic acid phosphate loaded 40/60 PCL/PLA film prepared using a prior art solvent casting process

Ascorbic acid phosphate (AZP) is a stable form of ascorbic acid having a melting temperature of about 260° C. Ascorbic acid phosphate is a white powder that is extremely hygroscopic. As received, the AZP can contain moisture up to about 7.5% by weight. Biocompatible, absorbable aliphatic polyester polymers are sensitive to moisture, which may cause degradation of the polymer especially at elevated temperatures. Attempts to melt blend AZP into absorbable aliphatic polyester polymers using conventional melt processing conditions have typically failed and yielded an unsuccessful result. The present invention provides a novel method of making controlled release compositions of ascorbic acid phosphate by melt processing. Controlled release compositions of ascorbic acid phosphate are useful in tissue repair and regeneration, and may be critical to the healing process for certain medical conditions and certain patients.

The novel controlled release compositions of ascorbic acid phosphate (AZP) of the present invention are prepared by drying AZP powder and melt blending the AZP powder with pre-dried biocompatible, absorbable aliphatic polyester polymer. The melt blended AZP/polymer composition may then be further melt processed into the form of the desired medical device or component including, but not limited to fibers, rods, screws, staples, suture anchors, films and the like. The melt processes that can be used to form such medical devices from the novel compositions of the present invention include conventional processes such injection molding, compression molding, extrusion and the like in accordance with the process requirements of the present invention. It is particularly preferred that the medical devices made from the control release compositions of the present invention are implantable into body tissues and/or body cavities, although they may be useful in external applications such as meshes or plates mounted to skin.

The term "controlled release" as used herein is defined as a sustained release of therapeutic agents with the control in time and space of the biological effects of therapeutic agents in human and animal health.

The term "burst" as used herein is defined as the initial high-rate drug release observed at the beginning of the controlled-release process. "Burst" can be caused by a number of mechanisms, including surface desorption, pore diffusion, or the lack of a diffusion front barrier to regulate the diffusive process. This initial nonsteady-state period may also be referred to as "burst release."

The term "absorbable polymers" as used herein is defined as synthetic, biocompatible polymers (including copolymers) that can degrade and be absorbed by the body when they are implanted in humans and animals. Absorbable polymers readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body.

In the process of the present invention, the AZP is dried to minimize bound water. The bound water is removed from the AZP by heating at a temperature of no greater than about 160° C. for about 30 minutes. The AZP is sufficiently dried to an amount to effectively prevent degradation of the polymer during processing. For example, the residual moisture is reduced to no more than about 1%. The AZP may be dried in a conventional manner using conventional drying apparatuses under vacuum or under inert atmosphere, such as nitrogen or argon gas. Although a material safety data sheet from an AZP manufacturer states that the degradation temperature of AZP is about 260° C., we discovered that drying the AZP at higher temperatures and longer times results in the progressive degradation of the AZP.

The absorbable aliphatic polyester polymers useful in the processes of the present invention must also be dried to minimize the moisture content prior to processing. The absorbable aliphatic polyester polymer may be dried in a conventional manner such as by storing under vacuum at room temperature until it is time for processing. The polymer may be kept dry in a conventional manner such as by storing under dry inert gas conditions.

Suitable absorbable aliphatic polyester polymers that may be used to prepare the AZP controlled release compositions as described herein are those having a melting temperature of no greater than 160° C., and are melt processable at a temperature of no greater than 160° C. Suitable absorbable aliphatic polyester polymers are homopolymers or copolymers prepared from monomers, including but not limited to lactide (including lactic acid), glycolide (including glycolic acid), epsilon-caprolactone, dioxanone, and trimethylene carbonate. In one embodiment, the absorbable aliphatic polyester polymers are prepared from monomers including, but not limited to epsilon-caprolactone, glycolide (including glycolic acid) and lactide (including lactic acid). In another embodiment, the absorbable aliphatic polyester polymer is a copolymer of epsilon-caprolactone and lactide having a molar ratio of about 40/60. In another embodiment, the absorbable aliphatic polyester polymer is a copolymer of epsilon-caprolactone and glycolide having a molar ratio of about 35/65.

The pre-dried AZP powder and absorbable aliphatic polyester polymer are weighed out and melt blended to form a composition under dry inert gas using a conventional melt blending machine, such as those sold under the tradename BRABENDER (Hackensack, N.J.). AZP may be added to the polymer in a sufficiently effective amount, for example, in the amount of about 0.5 wt. % to about 20 wt. % of the total weight of the composition. In one embodiment, AZP may be added to the polymer in the amount of about 2 wt. % to about 10 wt. % of the total weight of the composition. The dry AZP powder and absorbable aliphatic polyester polymer are then fed into a mixer preheated to a temperature of no greater than 160° C. and melt blended for about 5 minutes to about 30 minutes under dry inert gas to form an AZP/polymer composition. In one embodiment, the mixture is melt blended for about 5 minutes to about 15 minutes. In yet another embodiment, the mixture is melt blended for about 10 minutes.

The AZP/polymer composition may then be further processed into the controlled release composition in a suitable form or it may be granulated or pelletized and stored under dry conditions until ready for further processing into a the controlled release composition in a suitable form. Suitable forms of the controlled release composition are medical devices including, but not limited to fibers, rods, screws, staples, suture anchors, films and the like. Although not limited thereto, it is particularly preferred to process the compositions of the present invention into implantable medical devices and components, although the compositions may also be used for non-implantable devices and components. These forms or embodiments may be prepared by conventional melt processing methods, including s extrusion, injection molding, or by compression molding as long as the processing temperature is no greater than about 160° C.

In one embodiment, one or more bioactive agents may optionally be used in combination with the AZP controlled release compositions. The bioactive agents may be in or coated on the AZP controlled release compositions prepared as described herein.

Suitable bioactive agents include, but are not limited to agents that prevent infection (e.g., antimicrobial agents and antibiotics), agents that reduce inflammation (e.g., anti-inflammatory agents), agents that prevent or minimize adhesion formation, such as oxidized regenerated cellulose (e.g., those sold under the tradenames INTERCEED and SURGICEL, available from Ethicon, Inc.), and hyaluronic acid, and agents that suppress the immune system (e.g., immunosuppressants) heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types, chemotactic agents, antibiotics, and steroidal and non-steroidal analgesics.

A viable tissue can also be combined with the AZP controlled release compositions of the present invention to promote tissue regeneration. The source can vary and the tissue may have a variety of configurations, however, in one embodiment the tissue is optionally in the form of finely minced tissue fragments, which may enhance the effectiveness of tissue re-growth and encourage a healing response. In another embodiment, the viable tissue can optionally be in the form of a tissue slice or strip harvested from healthy tissue that contains viable cells capable of tissue regeneration and/or remodeling.

The AZP controlled release compositions can also be used in combination with cells to enhance collagen deposition. Suitable cell types include, but are not limited to, osteocytes, osteoblasts, osteoclasts, fibroblasts, stem cells, pluripotent cells, chondrocyte progenitors, chondrocytes, endothelial cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells.

One skilled in the art will appreciate that the identity of the bioactive agent may be determined by a surgeon, health care professional, or other life sciences professional, based on the principles of medical science and the applicable treatment objectives.

The AZP controlled release compositions of the present invention may be used in the following conventional surgical procedures where enhanced collagen synthesis is desired, including, but not limited to abdominal surgery, such as hernia repair and pelvic floor repair; dermal wound healing, cartilage repair, bone repair, ligament repair, and the like and equivalents, and any new procedures that might be developed wherein enhanced collagen synthesis is desired for an improved medical outcome.

The following examples are illustrative of the principles and practice of this invention, although not limited thereto. Numerous additional embodiments within the scope and spirit of the invention will become apparent to those skilled in the art once having the benefit of this disclosure.

EXAMPLE 1

AZP Drying Condition Evaluation

The following drying conditions for 2-Phospha-L-ascorbic Acid Trisodium Salt (AZP), (>98% (HPLC), Fluka, Lot#: 1322473 52607420) were tested: 90° C./24 hrs. under vacuum, 160° C./30 minutes under dry nitrogen blanket, and 200° C./30 minutes under dry nitrogen blanket. The times tested include estimating the compounding time and time for sample collection and cooling.

6 glass vials were pre-dried in a vacuum oven at 160° C. for 30 minutes and transferred to a glove box purged with dry nitrogen gas. AZP powder was weighed in each vial (see Table 1) in the glove box. The AZP powder vials were then subjected to heating conditions as shown in the Table.

TABLE

| Bottle # | Initial Weight (mg) | $1^{st}$ Heat for 24 hours (° C.)/ ($N_2$ or vac) | Weight after $1^{st}$ Heat (mg) | Weight loss after $1^{st}$ Heat (wt %) | $2^{nd}$ Heat for 30 min (° C.)/ ($N_2$ or vac) | Weight after $2^{nd}$ Heat (mg) | Total Weight loss after $2^{nd}$ Heat (wt %) |
|---|---|---|---|---|---|---|---|
| 1 (control) | 399 | RT/$N_2$ | 395 | 1.00 | RT/$N_2$ | 398 | 0.25 |
| 2 | 169 | RT/$N_2$ | 167 | 1.18 | 160/$N_2$/air | 152 | 10.06 |
| 3 | 284 | RT/$N_2$ | 279 | 1.76 | 200/$N_2$/air | 261 | 8.10 |
| 4 | 272 | 90/Vac | 250 | 8.09 | RT/$N_2$ | 260 | 4.41 |
| 5 | 224 | 90/Vac | 207 | 7.59 | 160/$N_2$/air | 210 | 6.25 |
| 6 | 311 | 90/Vac | 291 | 6.43 | 200/$N_2$/air | 290 | 6.75 |

The dried AZP powder vials were sealed with Parafilm and stored under dry a nitrogen blanket until evaluation. The weight loss % was cumulative over both heating conditions. The samples under RT/$N_2$ were stored in nitrogen box. The samples were evaluated for color change of the course of the heating conditions. Color change is an indicator of AZP degradation. The samples heated for no more than 30 minutes retained the original white color of the AZP powder. The samples heated at 90° C./24 hrs. treatment showed a very slight yellow color, therefore heating for long times even at a lower temperature was observed to cause some degradation of the AZP. The samples that underwent 2 heat treatments changed to a slightly yellow color. The sample number 6 heated to 200° C. had the darkest yellow color. It appeared that the drying is complete under 90° C./vacuum/24 hrs., since the further drying at higher temperatures did not cause a decrease in weight. The higher temperature and shorter time could have the same drying effects on the weight loss. The minimum weight change of the control sample showed that the handling process was reasonable. Therefore 160° C. and 30 minutes were selected as the upper limits of the drying and processing condition The finalized drying process is as follows: the oven is pre-heated to 160° C. under dry nitrogen blanket; an 8-OZ. vial and its cap were dried by heating at 160° C. for 30 min. transferred to a glove box purged with dry nitrogen and weighed; in the glove box the AZP was weighed into the vial; the AZP vial was placed in the oven for 30 minutes; the vial was shaken once at about the 15 minute point; the AZP vial was capped and sealed in the oven with its pre-dried cap; the capped AZP vial was removed from the oven and weighed.

The AZP weight and the weight loss percentage was calculated. The AZP vial was stored under dry nitrogen atmosphere until ready for processing.

EXAMPLE 2

Comparison of Solvent-Cast Film Formulation and Evaluation

In a glove box under dry nitrogen blanket, a quantity of 32 milligrams of AZP that was pre-dried at 160° C./30 min as described in Example 1, was weighed into a 20-ml bottle. 9.0 ml of $CH_2Cl_2$ were immediately added to the bottle using a syringe and the bottle was capped. The AZP solution was removed from the glove box and was sonicated for 10 minutes. The solution was returned to the glove box where 0.6 grams of 40/60 PCL/PLA polymer (lot# D99069, Birmingham Polymer, Inc.) were then added to the AZP solution and capped again. The mixture was removed from the glove box and shaken at room temperature until the polymer fully dissolved. A solvent cast film was prepared by pre-cooling the shelves of a VirTic lyophilizer (Model: AdVantage, MFR: VirTic) to 6° C. The AZP/polymer solution was poured into a 5 cm×5 cm teflon-coated metal mold, then immediately transferred to the pre-cooled shelf. The slow evaporation proceeded with nitrogen blanket to prevent water condensation. After the solvent was removed, the film having a thickness of about 150 microns to 200 microns was collected and stored under vacuum for follow-up process or/and characterization.

8 mm discs were punched from the solvent-cast film using dermal biopsy punches. A disc was then transferred into an HPLC vial. 2 mLs of phosphate buffered saline (PBS) (pH=7.4) were added to each vial. The vials were incubated in a heated, shaking water bath at 37° C. and 100 rpm. At each time point, the release medium was removed and replaced with 2 ml of fresh PBS. AZP in the release medium was measured using HPLC. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. The release profile is shown in FIG. 1.

Prior art formulations of an ascorbic acid phosphate controlled release systems using solvent casting have met with limited success. As shown in FIG. 1, the prior art ascorbic acid phosphate in 40/60 (mol/mol) PCL/PLA films prepared by solvent casting showed a high burst of up to 40 weight % of the total amount of AZP in the composition. The undesirable high burst is due to the hydrophilic nature of AZP and the porosity created in the film by solvent evaporation.

EXAMPLE 3

Preparation and Evaluation of AZP/(25/75 PCL/PGA) Film at a Processing Temperature of 200° C.

AZP/polymer compositions were prepared as follows: In a glove box purged with dry nitrogen, a 2 wt % of AZP/polymer composition was prepared by weighing 30.4 grams of 25/75 PCL/PGA polymer (Lot# UAZC020, Ethicon) and 0.63 grams of AZP that was pre-dried at 160° C./30 min as described in Example 1, into a container and dry mixed together. Meanwhile, A 30-ml Brabender mixer (Model: R.E.E.6/2, C.W. Brabender Instruments, Hackensack, N.J.) was pre-heated to 200° C. A dry nitrogen blanket was maintained. The mixer was set at a speed of 30 rpm. The AZP/polymer mixture was quickly transferred from the glove box and into the mixer and closed. The materials were allowed to mix for about 10 minutes. Mixing was stopped and the AZP polymer composition was collected. The composition was stored under vacuum until ready for further processing into the controlled release composition.

Films were prepared as follow: The platens of a compression molding instrument (Carver Laboratory Press, Model: 2696) were pre-heated to 205° C. About 3.5 grams of the composition were placed on the platens and heated for 5 minutes. Pressure was applied (about 20,000 lbs) for about 2 minutes. The heating was stopped and the platens and film were allowed to cool to RT under water cooling and continued pressure. The film was intact having a thickness of about 150 microns to 200 microns but it was brown in color indicating degradation.

AZP recovery was determined using an HPLC assay. A 121 mg of film was transferred into a 50-ml volumetric flask. 10 ml of HFIP was added to the flask, & stirred. After the sample was fully dissolved, DI water was added dropwise to fill the flask to the mark. The solution was filtered through a 0.2 micron syringe filter before HPLC analysis. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. The recovery rate of AZP was less than 1%.

The melting temperature of ascorbic acid phosphate is 260° C. One may assume that any polymers that can be thermally processed at temperatures lower than 260° C. could be used for the composition of controlled release compositions using a melt blending process. Surprisingly, we discovered that thermal processing of a combination of dry AZP and absorbable polymer at 200° C. caused almost complete degradation of the AZP. In contrast, as shown below in Examples 4 and 5, films prepared at a processing temperature of no greater than about 160° C. showed a dramatic increase in AZP recovery from the films.

EXAMPLE 4

Preparation and Evaluation of AZP/(40/60 PCL/PLA) Film Prepared at a Processing Temperature of 160° C.

AZP/polymer compositions were prepared as follows: In a glove box purged with dry nitrogen, a 2 wt % of AZP/polymer composition was prepared by weighing 30.4 grams of 40/60 PCL/PLA polymer (Lot# UAZC020, Ethicon, Inc, Somerville, N.J.) and 0.63 grams of AZP that was predried at 160° C./30 min as described in Example 1, into a container and dry mixed together. The AZP/polymer was mixed under a dry nitrogen blanket. A 30-ml Brabender mixer (Model: R.E.E.6/2, C.W. Brabender Instruments Hackensack, N.J.) was pre-heated to 160° C. A dry nitrogen blanket was maintained. The mixer was set at a speed of 30 rpm. The AZP/polymer mixture was quickly added into the mixer and closed. The materials were allowed to mix for about 10 minutes. Mixing was stopped and the AZP polymer composition was collected. The composition was stored under vacuum until ready for further processing into the desired for the controlled release composition. This process was repeated to prepare 5 wt % and 10 wt % AZP/polymer compositions.

Films were prepared using 2 wt %, 5 wt %, and 10 wt % AZP polymer compositions as follows: The platens of a compression molding instrument (Carver Laboratory Press, Model: 2696, Wabash, Ind.) were pre-heated to 160° C. About 3.5 grams of the composition were placed on the platens and heated for 5 minutes. Pressure was applied (about 20,000 lbs) for about 2 minutes. The heating was stopped and the platens and film were allowed to cool using water cooling to RT under the pressure. The film was collected having a 150 micron to 200 micron thickness and stored under dry nitrogen until ready for testing.

Figure 2:
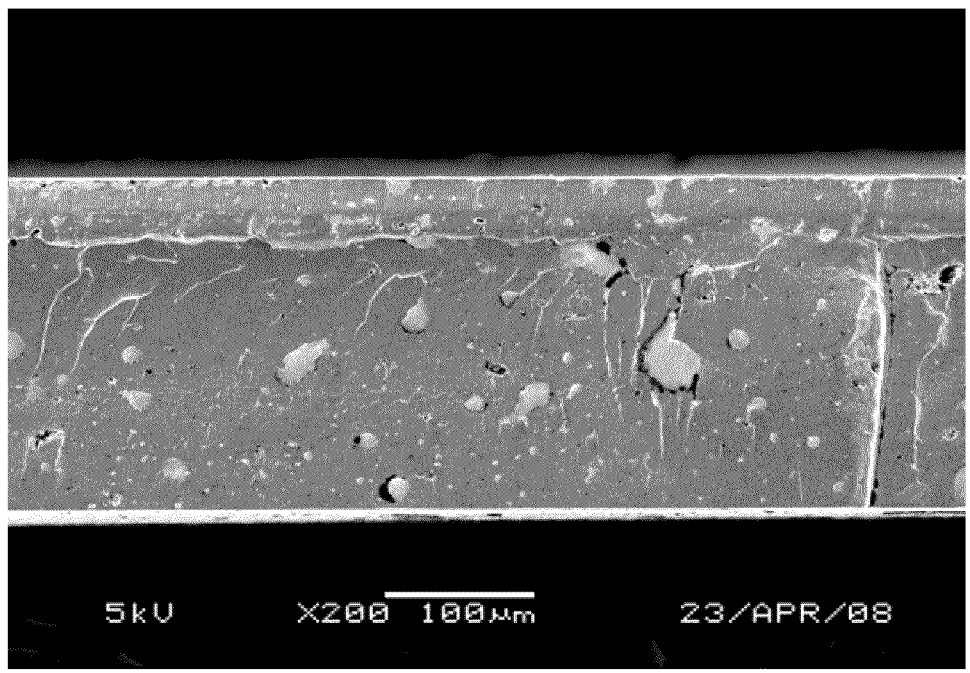
FIG. 2 shows an SEM image of a cross section of an ascorbic acid phosphate loaded 40/60 PCL/PLA film prepared as described in Example 3.

A piece of the film was trimmed in cross section, mounted on a microscope stud, and coated with a thin layer of gold using an EMS 550 sputter coater (Electron Microscopy Sciences, Hatfield, Pa.). SEM analysis was performed using the JEOL JSM-5900LV SEM (JEOL, Tokyo, Japan). The surfaces and cross-sectional areas were examined for each sample. The SEM images showed that the AZP particles are embedded and uniformly distributed in the film. See an exemplary SEM micrograph in FIG. 2.

AZP Recovery was determined using an HPLC assay. AZP Recovery was determined using an HPLC assay. A 27 mg of sample was transferred into a 50-ml volumetric flask. 10 ml of dioxane was added to the flask and stirred with gentle heat at 30-50° C. After the sample was fully dissolved, DI water was added dropwise to 50 mL to fill the flask to the mark. The solutions were filtered through a 0.2 micron syringe filter before HPLC analysis. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. Dried AZP treated in the same way as the film was used as a control. The recovery of AZP from a film loaded with 10 wt. % AZP was about 84% by weight. The AZP recovery from a film loaded with 5 wt. % AZP was measured using the same method. The recovery was 78%.

Figure 3:
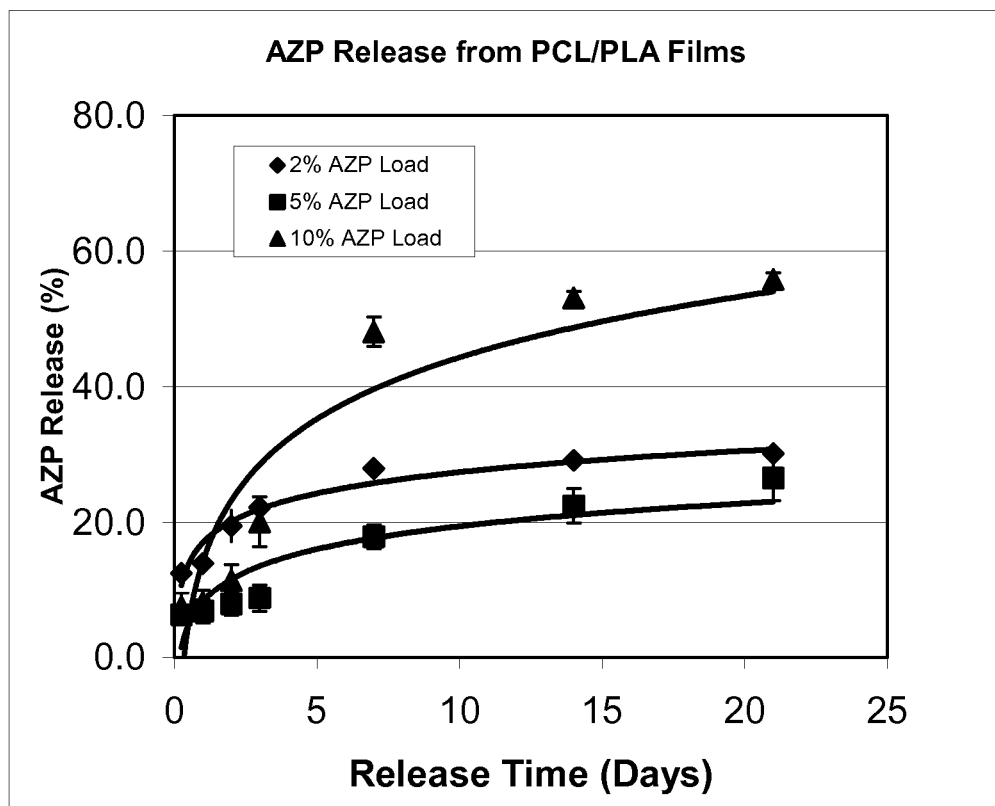
FIG. 3 shows a release profile of ascorbic acid phosphate loaded 40/60 PCL/PLA film prepared as described in Example 5.

Release of AZP from the AZP/polymer films was determined by the following method: 10 mm discs were punched from the films using dermal biopsy punches. A disc was then transferred into an HPLC vial. 1.5 mLs of phosphate buffered saline (PBS) (pH=7.4) were added to each vial. The vials were incubated in a heated, shaking water bath at 37° C. and 100 rpm. At each time point, the release medium was removed and replaced with 2 ml of fresh PBS. AZP in the release medium was measured using HPLC. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. The release profile is shown in FIG. 3.

EXAMPLE 5

Preparation of AZP/(35/65 PCL/PGA) Films at a Processing Temperature of 130° C.

AZP/polymer compositions were prepared as follows: In a glove box purged with dry nitrogen, a 2 wt % AZP/polymer composition was prepared by weighing 30.4 grams of 35/65 PCL/PGA polymer (Lot# UAZC020, Ethicon) and 0.63 grams of AZP that was predried at 160° C./30 min as described in Example 1, into a container and dry mixing together. Meanwhile, a 30-ml Brabender mixer (Model: R.E.E.6/2, C.W. Brabender Instruments) was pre-heated to 130° C. A dry nitrogen blanket was maintained. The mixer was set at a speed of 30 rpm. The AZP/polymer mixture was quickly transferred from the glove box into the mixer and closed. The materials were allowed to mix for about 10 minutes. Mixing was stopped and the AZP polymer composition was collected. The composition was stored under vacuum until ready for further processing into the controlled release composition. This process was repeated to prepare 5 wt % and 10 wt % AZP/polymer compositions.

Films were prepared using 2 wt %, 5 wt %, and 10 wt % AZP/polymer compositions as follows: The platens of a compression molding instrument (Carver Laboratory Press, Model: 2696 Wabash, Ind.) were pre-heated to 130° C. About 3.5 grams of the composition were placed on the platens and heated for 5 minutes. Pressure was applied (about 20,000 lbs) for about 2 minutes. The heating was stopped and the platens and film were allowed to cool using water cooling to RT under the pressure. The film was collected having a thickness of 150 to 200 microns and stored under dry nitrogen conditions until ready for testing.

Figure 4:
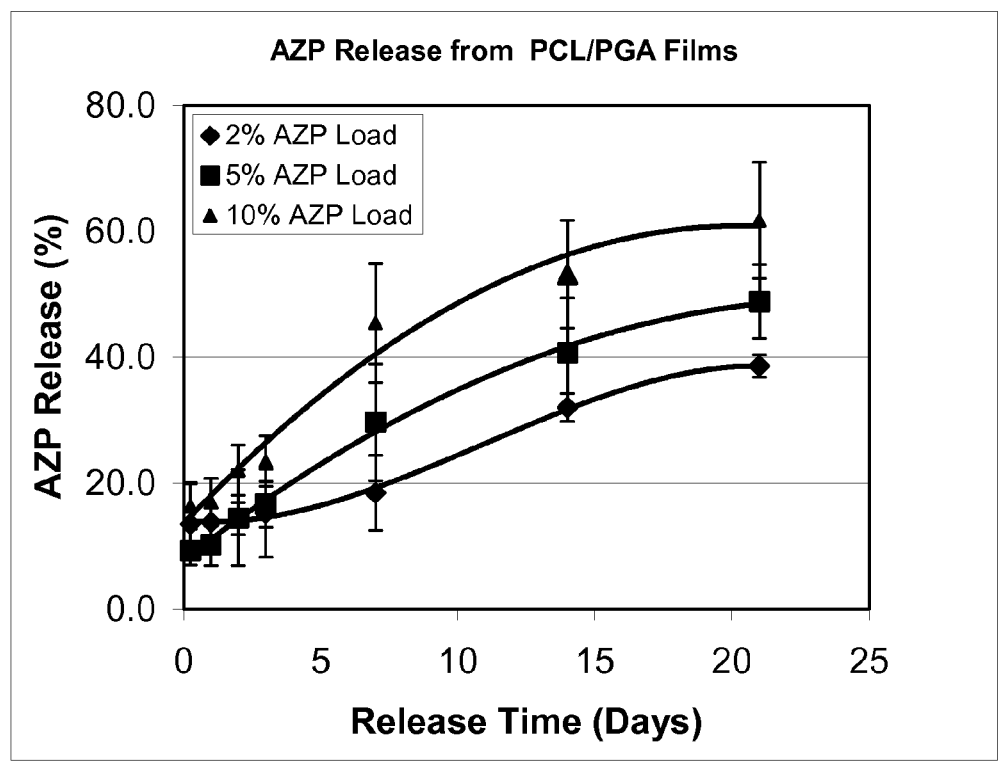
FIG. 4 shows a release profile of ascorbic acid phosphate loaded 35/65 PCL/PGA film prepared as described in Example 4.

AZP Recovery was determined using an HPLC assay. A 50 mg of film was transferred into a 50-ml volumetric flask. 10 ml of dioxane was added to the flask and stirred with gentle heat at 30-50° C. After the sample was fully dissolved, DI water was added dropwise to fill the flask to the mark. The solutions were filtered through a 0.2 micron syringe filter before HPLC analysis. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. Dried AZP treated in the same way as the film was used as a control. The recovery of AZP from films loaded with 5 wt % AZP was about 92%. Release of AZP from the AZP/polymer films was determined by the following method: 10 mm discs were punched from the films using dermal biopsy punches. A disc was then transferred into an HPLC vial. 1.5 mLs of phosphate buffered saline (PBS) (pH=7.4) were added to each vial. The vials were incubated in a heated, shaking water bath at 37° C. and 100 rpm. At each time point, the release medium was removed and replaced with 2 ml of fresh PBS. AZP in the release medium was measured using HPLC. HPLC was performed using a Gemini column (Phenomenex, Torrance, Calif., USA) with a Model 2695 HPLC system (Waters, Milford, Mass., USA) with a PDA detector. UV absorption at 238 nm was measured. An isocratic mobile phase containing 5 mM KH2PO4, 6 mM H3PO4, 12 mM tetrabutylammonium hydrogen sulfate, 10% methanol, pH 2.5 was used. The flow rate was 1 ml/min. A stock AZP standard was prepared by dissolving 5 mg of AZP in water in a 10-ml volumetric flask and mixing thoroughly. The stock solution was diluted 1:10 and 1:100 before use. The release profile is shown in FIG. 4.

The method of manufacturing AZP compositions of the present invention and the novel compositions manufactured by this method have many advantages. The advantages include a more desirable release profile of AZP with low burst release of less than 20 wt % followed by a sustained release. Sustained release is over a period of 1 week or greater. In one, embodiment the sustained release is about 3 weeks or more. Another advantage is suitability for producing various geometrical shapes of devices, and better mechanical properties than solvent cast methods, and the availability of a broad material selection including soluble and insoluble materials in solvents that can be safely used for processing.

Although this invention has been shown and described with respect to detailed embodiments thereof, it will be understood by those skilled in the art that various changes in form and detail thereof may be made without departing from the spirit and scope of the claimed invention.

We claim:

1. A controlled release composition, comprising:
   a controlled release composition of ascorbic acid phosphate manufactured by the method comprising:
   drying ascorbic acid phosphate at a temperature of no greater than 160° C. for about 30 min; and,
   melt blending the dried ascorbic acid phosphate with an absorbable aliphatic polyester polymer at a temperature of no greater than about 160° C., thereby forming the ascorbic acid phosphate and polymer composition.

2. The composition of claim 1, wherein the process comprises the additional step of processing the ascorbic acid and polymer composition into a desired form at a temperature of no greater than about 160° C.

3. The composition of claim 1, wherein the composition comprises ascorbic acid phosphate in the amount of about 0.5 wt % to about 20 wt %.

4. The composition of claim 1, wherein the composition comprises ascorbic acid phosphate in the amount of about 2 wt % to about 10 wt %.

5. The composition of claim 1, wherein the absorbable aliphatic polyester polymer is a homopolymer or copolymer prepared from monomers selected from the group consisting of lactide, glycolide, epsilon-caprolactone, dioxanone, and trimethylene carbonate.

6. The composition of claim 1, wherein the absorbable aliphatic polyester polymer is a copolymer prepared from epsilon-caprolactone and glycolide.

7. The composition of claim 2, wherein the composition is formed into a medical device selected from the group consisting of fibers, rods, screws, staples, suture anchors, films and combinations thereof.

8. The composition of claim 1, wherein the absorbable polymer and the ascorbic acid phosphate are melt blended for about 5 minutes to about 30 minutes.

9. The composition of claim 1, wherein the composition additionally comprises at least one bioactive agent.

10. The composition of claim 1, wherein the composition additionally comprises viable tissue.

11. A medical device, comprising:
    a controlled release composition of ascorbic acid phosphate manufactured by the method comprising:
    drying ascorbic acid phosphate at a temperature of no greater than 160° C. for about 30 min; and,
    melt blending the dried ascorbic acid phosphate with an absorbable aliphatic polyester polymer at a temperature of no greater than about 160° C., thereby forming the ascorbic acid phosphate and polymer composition.

* * * * *